United States Patent [19]

MacDonald

[11] Patent Number: 4,532,089
[45] Date of Patent: Jul. 30, 1985

[54] METHOD OF PREPARING GIANT SIZE LIPOSOMES

[75] Inventor: Robert C. MacDonald, Evanston, Ill.

[73] Assignee: Northwestern University, Evanston, Ill.

[21] Appl. No.: 570,950

[22] Filed: Jan. 14, 1984

[51] Int. Cl.³ .......................... B01J 13/02; A61K 9/52
[52] U.S. Cl. ..................................... 264/4.3; 264/4.1; 424/38; 428/402.2; 436/829
[58] Field of Search ............................... 264/4.1, 4.3; 428/402.2; 424/38; 436/829

[56] References Cited

U.S. PATENT DOCUMENTS

| 3,957,971 | 5/1976 | Oleniacz | 424/343 X |
| 4,016,100 | 4/1977 | Suzuki et al. | 264/4.3 |
| 4,133,874 | 1/1979 | Miller et al. | 424/38 |

OTHER PUBLICATIONS

Huntress: *The Preparation, Properties, Chemical Behavior, and Identification of Organic Chlorine Compounds,* John Wiley & Sons, Inc., New York, (1948), pp. 138–141.

Kasahara et al.: "Reconstitution and Purification of the D-Glucose Transporter from Human Erythrocytes", J. Biol. Chem., 252, (1977): 7384–7390.

Pick: "Liposomes with a Large Trapping Capacity Prepared by Freezing and Thawing of Sonicated Phospholipid Mixtures", Arch. Biochem. Biophys., (1981), 212: 186–194.

*Primary Examiner*—Richard D. Lovering

[57] ABSTRACT

Large size liposomes are produced from small unilamellar vesicles by incorporating a polar compound in an aqueous dispersion of the vesicles, subjecting the dispersion to repeated freeze-thaw cycles, and thereafter dialyzing the vesicles against a hypoosmotic medium. The freeze-thaw cycles aggregate the vesicles and increase their internal concentration of polar compound. During dialysis the vesicles imbibe water, rupture, and form enlarged liposomes.

17 Claims, No Drawings

METHOD OF PREPARING GIANT SIZE LIPOSOMES

FIELD OF INVENTION, BACKGROUND AND PRIOR ART

The field of this invention is the production of large size lipid vesicles or liposomes. In particular, the invention is concerned with the production of giant size liposomes from small unilamellar vesicles (SUV) by a freeze-thaw manipulation of the SUV aqueous dispersions.

Processes have heretofore been described for producing larger sizes of liposomes in which SUV produced by sonication are induced to enlarge by fusion in the presence of calcium ions, or by techniques utilizing organic solvents or detergents. The calcium-fusion method is limited to certain lipids. The production of large unilamellar liposomes by using organic solvents or detergents has its limitations for entrapping biological agents, since such agents may be activated by the solvent or detergent.

In 1977, Kasahara and Hinkel described a procedure which produced enlargement of liposomes, consisting of an initial sonication followed by freezing, thawing, and a further brief sonication (*J. Biol. Chem.* 252: 7384–7390). Subsequently, Pick described further experiments in which liposomes with a large trapping capacity were prepared by freezing and thawing of sonicated phospholipid mixtures. *Arch. Biochem. Biophys.* (1981) 212: 186–194. Pick estimated that the maximal trapping efficiency of the procedure was about 25–30% of the ambient solution, and further found that a number of conditions inhibited enlargement and maximized trapping. These included increasing the ionic strength of the medium and/or increasing the liposome concentration. Pick was also unable to obtain satisfactory enlargement of the vesicles using purified egg phospholipid (phosphatidylcholine).

SUMMARY OF THE INVENTION

The present invention provides a greatly improved freeze-thaw process for vesicle enlargement, as compared with the closest known prior art disclosures of Kasahara and Hinkel (1977) and Pick (1981), cited above. With the process improvements of the present invention, it is beneficial for maximized vesicle enlargement and trapping to use a high (relative to the final desired solution) osmolarity of solute which may be a common electrolyte such as KCl, a chaotropic electrolyte such as potassium trichloroacetate, a crystallizable (from aqueous solution) non-electrolyte such as urea.

The improved method is generally applicable to bilayer-forming liposomes including purified egg phospholipid. Much larger vesicles can be obtained than those prepared by published prior art process. In certain embodiments, liposomes produced by the method of this invention have diameters of tens of micrometers (viz. 10–50 μm). Entrapment volumes of more than 5 microliters/mg lipid can easily be obtained, and entrapping efficiencies up to nearly 100% of the ambient solution are possible.

The resulting liposomes are stable, and can be used for a variety of known purposes, such as analytical reagent and drug carriers. Substances such as enzymes which would be inactivated by organic solvents and detergents can usually be encapsulated without degradation. The process is simple, positive in results, and well adapted for production of very large size liposomes on a commercial basis.

DETAILED DESCRIPTION

The method of this invention is believed to be generally applicable to bilayer-forming lipids, including phospholipids and glycolipids. It has been demonstrated with egg yolk phospholipid as well as with defined mixtures of pure phospholipid. The freeze-thaw procedure used as part of the present invention has been employed by the prior art workers with other lipids, and can be used herein. See Kasahara et al. (1977) *J. Bio. Chem.* 252: 7384–7390; and Pick (1981) *Arch. Biochem. Biophys.* 212: 186–194. Literature references identify additional bilayer-forming lipids which can be used in the method of the present invention. Compilations are found in Gregoriadis (1976) *N. Engl. J. Med.* 295: 704–710, 765–770; and Szoka et al. (1980) *Ann. Rev. Biophys. Bioeng.* 9: 467, at 469–476.

The small unilamellar vesicles (SUV) used as the starting material for the method of this invention can be prepared by well known procedures. For example, SUV may be formed by sonication of MLV produced by the method originally described by Bangham et al. (1965), namely, hydration of an anhydrous lipid phase. (*J. Mol. Biol.* 13: 238–252). The SUV are microvesicles with sizes as small as 200 Angstroms. Such SUV dispersions in water can be formed without the presence of other reagents besides the lipid or a mixture of lipids. The dispersion during formation of the SUV should be above the transition temperature (Tc) of the lipid, or, if a mixture of lipids is employed, above the transition temperature of the lipid component of the mixture having the highest Tc. Under such temperature conditions, the lipids are in fluid condition so that upon hydration the bilayer unilamellar vesicles can form.

For the purpose of this invention, it has been found desirable to employ somewhat higher lipid concentrations in the dispersion than have been conventional in most prior art procedures. The lipid concentration should be at least 1% by weight of the dispersion, and preferably at least 2%. Higher lipid concentrations up to as high as 10% or more can be profitably employed.

After formation of the SUV dispersion and prior to subjecting the dispersion to freezing, a water-soluble crystallizable polar compound is dissolved in the external water phase of the dispersion. A solution concentration of at least 0.1 molar should be used, and in preferred embodiments, a concentration of at least 0.5 molar is employed, the upper limit being the saturation concentration of the solute at the temperature of the dispersion. Typical concentrations range from about 0.5 to 2.5 molar. For example, concentrations of 1 molar or 2 molar are usually advantageous. When the solute is a potent chaotrope such as potassium trichloroacetate, concentrations may be lowered as much as 10 times.

Assuming that the substance that is to be entrapped is not the crystallizable compound itself, that is, because of inadequate concentration or lack of crystallizability, would not function to generate giant vesicles by itself, it is included along with the crystallizable solute at the appropriate concentration. In choosing the appropriate concentration it should be recognized that the osmotic inflation process will normally cause the vesicle contents to be diluted by the ratio of the total osmolarity after freezing and thawing to the osmolarity of the solution against which dialysis is performed.

The crystallizable compound may be ionizable or nonionizable, and may be inorganic or organic. For example, soluble metal salts may be used, such as alkali metal halides, nitrates, sulfates, etc. In the experimental work leading to the present invention, excellent results was obtained using potassium or rubidium chlorides, or a mixture of cesium and calcium chlorides. The eutectic freezing temperatures of saturated solutions of these salts are obtainable with dry ice cooling. Where the saturated solutions of the electrolytes saturated lower eutectic temperatures, such as for sodium and lithium chloride solutions, a greater degree of refrigeration may be required to achieve complete freezing, viz. the use of liquid nitrogen as the freezing agent. Similarly, certain crystallizable organic compounds appreciably lower the freezing temperature of the water, requiring a greater degree of refrigeration. The crystallizable compounds should not be of a kind or used in such an amount that it will prevent complete freezing of the dispersion. Another class of solute is chaotropic electrolytes such as the potassium salts of tribromoacetate and trichloroacetate.

As the temperature of the dispersion is reduced during the freezing step, the aqueous phase external to the vesicles becomes saturated with the crystallizable compound. With further temperature reduction, the compound crystallizes. At the same time, ice crystals are being formed, which may be either pure water, or combined in crystalline form with the polar compound. Where the mixture has a eutectic, both types of crystals will be generated during the freezing process. In general, it is preferred to reduce the temperature in the freezing step sufficiently to crystallize all of the water.

With the increasing concentration of the polar compound during the freezing step, water will be osmotically extracted from the vesicles, and it may be expected that the edges of the resultant flattened disks may become unstable because of small radii of curvature. The generation of the ice crystals will have a packing effect on the vesicles, forcing them into closer contact. This results in adhesion and aggregation of the vesicles. After several freeze-thaw cycles, the vesicles become highly aggregated. The vesicle population is heterogenous, varying in size and degree of aggregation, and both unilamellar and mutilamellar vesicles are believed to be present. The freeze-thaw process does create some vesicles of enlarged size by disruption and fusion of the vesicle walls. However, further processing is required to obtain a large number of vesicles. In the thawing step, the temperature is preferably raised until substantially all of the ice crystals have melted. It is not necessary, however, to resolubilize all of the crystallized polar compound before repeating the freeze-thaw cycle. Both the freezing and thawing steps may be carried out rapidly.

In the case of chaotropic solutes, additional effects may come into play; as the solute becomes concentrated by freezing out of the water, the chaotrope reduces the integrity of vesicle wall, allowing capture of both the chaotrope and the substance that is desired to be entrapped. The vesicle may even substantially disintegrate, in which case entrapment occurs when vesicles reform upon thawing as the chaotrope becomes diluted again.

The time required for freezing may range from about 1 to 7 minutes, and the thawing step may likewise take from about 1 to 7 minutes. If desired, however, the freeze-thaw cycles may be carried out more slowly.

Repetition of the freeze-thaw cycles is desirable, and, in general, the freeze-thaw cycles are repeated until the resulting vesicles are in an aggregated form and contain entrapped high concentration solution. For example, from 3 to 10 freeze-thaw cycles may usefully be employed.

During the freeze-thaw cycles, the vesicles are disrupted and reformed, resulting in a mixture of unilamellar, multilamellar, and aggregated vesicles, containing both the crystallizable polar compound that provides, in the usual case, the major contribution to the total osmolarity, as well as any substance desired to be entrapped such as a protein, nucleic acid, or fluorescent dye. The reformed vesicles will have trapped solution of a higher concentration up to the saturation concentration. Since the reformed vesicles are relatively impermeable to the polar compound, the high concentration will be retained within the vesicles. As the concentration of the external phase decreases and returns to the starting concentration, water osmotically passes into the vesicles, reducing their interior concentration and swelling the vesicles. These aggregated higher concentration vesicles are then used in the next step of the process to prepare the giant size unilamellar vesicles.

The aggregated, high internal concentration vesicles may be retained in the thawed dispersion and subjected to dialysis therein. The particular dialysis procedure and equipment is not critical. The primary requirement is that the vesicles be dialyzed against a hypoosmotic solution. For example, water can be used as the dialysis medium. The vesicles because of their high interior concentration will rapidly imbibe water, which will cause the vesicles to swell, rupture, and reform. As the process continues, the vesicle aggregates are converted into a greatly enlarged unilamellar form.

In one advantageous procedure, the thawed dispersion of the aggregated vesicles is introduced into a flexible dialysis bag, and the bag is placed in the dialysis medium. The temperature of the dialysis should be above the transition temperature (Tc) of the lipid. Where the vesicles have been formed from a mixture of lipids of different transition temperatures, the temperature of the dialysis should be above the Tc of the lipid component having the highest Tc.

As the dialysis proceeds within the dialysis bag, the enlarging of the vesicles can result in an appreciable packing effect. This is believed to further promote the enlargement process. The solution capture efficiency is very high, the vesicle enlargement during dialysis can be carried to a point where 50% or more dialysis bag volume is entrapped. With concentrations of lipid in the starting SUV dispersion in the range of 3 to 5% by weight, the vesicle enlargement may be carried to 10 microliters trapped volume per mg lipid or higher. After formation of the enlarged unilamellar vesicles, as described, the resulting liposome product is relatively stable, and can be stored in the refrigerator for months if precautions are taken to prevent bacterial growth.

The method of this invention is further illustrated by the following examples.

EXAMPLE I

Typical Recipe

50–100 mg of egg phospholipids are dispersed in distilled water by sonication for several minutes with a probe-type sonicator or until most of the vesicles have been reduced to diameters of 500 Angstroms or less.

KCl is added to saturation and any other substance desired to be entrapped is added to this solution. For example, the fluorescent dye, calcein may be added at concentrations up to a few hundred millimolar. The suspension is immersed in a dry ice-alcohol both for several minutes or until completely frozen. The sample is then thawed, conveniently under warm water. The freeze-thaw procedure is repeated at least twice for good results and up to 10 times for optimum results. The suspension of lipid vesicles is then placed in a 1.5 in. section of 1 cm dialysis tubing and dialyzed against several hundred ml of 0.1M NaCl or KCl buffered as appropriate. Dialysis is carried out over night at room temperature. For optimum results the dialysate is changed two or three times and the sample is transferred to a larger piece of dialysis tubing each time it is found to be turgid. The aqueous volume inside vesicles at the end of the procedure will be at least 10 $\mu l/\mu$mole of lipid and several percent of the lipid will form vesicles of several microns or more in diameter.

EXAMPLE II

Effect of Multiple Freeze-Thaw Steps 10 mg egg yolk phospholipid is sonicated in 1 ml water and the suspension made 1M in KCl containing a trace of calcium (for volume determination). It is frozen and thawed from 0 to 10 times and dialyzed overnight against 10mM MOPS buffer. The suspension is analyzed for numbers of vesicles with diameters >5 microns and for entrapped aqueous volume according to established procedures (Oku and MacDonald, *Biochemistry* 22: 855-863, 1983.). Both numbers of large vesicles and trapped volume increase with the number of freeze-thaw cycles and only begin to plateau at 10 cycles.

EXAMPLE III

Need for Hyposmolar Dialysis

Egg phospholipids (10mM) in 0.3M KCl (+0.1mM calcium for volume determination) were frozen and thawed for 3 cycles. After freezing and thawing and after subsequent dialysis against (1) 10mM MOPS buffer or 0.3M KCl, trapped volume and number of vesicles with diameters >5 microns were determined (Oku and MacDonald, *Biochemistry* 22: 855-863, 1983). Giant vesicles (diameters >5 microns diameter) are observed only in the case of dialysis against the hyposmoeter 10mM MOPS solution.

EXAMPLE IV

Polar Crystallizable Solutes Other Than KCl

The procedure of Example II may be followed substituting 0.1M or higher concentration of potassium trichloroacetate or 2.4M or higher concentration of urea for 1M KCl. By extrapolating from the results in KCl, the preparation may be further improved by using higher concentrations of lipids and enlarging the dialysis bag several times during dialysis.

I claim:
1. An improvement in the method of treating aqueous dispersions of small unilamellar vesicles (SUV) to obtain vesicles of enlarged size, said SUV having been prepared by hydration of a bilayer-forming lipid, and thereafter subjecting said aqueous dispersion to at least one cycle of freezing and thawing, wherein the improvement comprises:
   (a) having present in said SUV dispersion prior to said freeze-thaw cycle at least a 0.1 molar concentration of a crystallizable polar compound plus any additional substance desired to be entrapped in large vestices;
   (b) then subjecting the dispersion to repeated freeze-thaw cycles in which the temperature reduction in the freezing step is sufficient to crystallize substantially all of the water, said freeze-thaw cycles being repeated until the resulting vesicles are in a generally aggregated form and contain entrapped solution of increased polar compound concentration as well as other substances desired to be entrapped; and then
   (c) dialyzing the resulting vesicles against an aqueous hypoosmotic medium causing the vesicles to imbibe water, said dialysis being continued until said aggregated vesicles imbibe sufficient water to reform into enlarged unilamellar vesicles.

2. The method of claim 1 in which said SUV dispersion has a lipid concentration of at least 1% by weight.

3. The method of claim 1 in which said lipid is a phospholipid.

4. The method of claim 1 in which said polar compound is present in a concentration of at least 0.5 molar.

5. The method of claim 1 in which during the dialysis step (c) vesicles enlarge to entrap a total of at least 5 microliters of water per mg lipid.

6. The method of claim 1 in which the lipid concentration in said SUV dispersion is from 3 to 10% by weight.

7. The method of claim 1 in which said polar compound is an alkali metal salt.

8. The method of claim 1 in which said polar compound is a potassium salt.

9. The method of claim 1 in which said polar compound is a salt of a chaotropic anion chosen from the group consisting of tribromoacetate and trichloroacetate.

10. The method of claim 1 in which said polar compound is a polar non-electrolyte having a solubility in water greater than 0.1M.

11. The method of treating aqueous dispersions of small unilamellar vesicles to obtain vesicles of enlarged size, said vesicles having been prepared by hydration of a bilayer-forming phospholipid, the phospholipid content of said dispersion on a water-lipid basis being at least 1% by weight, comprising dissolving in said dispersion a water-soluble polar compound to a concentration of at least 0.1 molar, subjecting to the polar compound-containing dispersion to repeated freeze-thaw cycles until the resulting vesicles are in a generally aggregated form and contain entrapped solution of increased polar compound concentration, and then dialyzing the resulting vesicles against an aqueous hypoosmotic medium causing the vesicles to imbibe water, said dialysis being continued until said aggregated vesicles have imbibed sufficient water to reform into enlarged unilamellar vesicles.

12. The method of claim 11 in which said polar compound is present in a concentration of at least 0.5 molar.

13. The method of claim 11 in which the lipid concentration in said dispersion is from 3 to 10% by weight.

14. The method of claim 11 in which said polar compound is potassium chloride.

15. The method of claim 11 in which said polar compound is the salt of a chaotropic anion chosen from the group consisting of tribromoacetate and trichloroacetate.

16. The method of claim 11 in which said polar compound is a polar non-electrolyte having a solubility in water exceeding 0.1 molar.

17. The method of claim 11 in which said lipid vesicles during said dialysis enlarge to entrap a total of at least 10 microliters per mg lipid.

* * * * *

UNITED STATES PATENT AND TRADEMARK OFFICE
CERTIFICATE OF CORRECTION

PATENT NO. : 4,532,089
DATED : July 30, 1985
INVENTOR(S) : Robert C. MacDonald

It is certified that error appears in the above-identified patent and that said Letters Patent is hereby corrected as shown below:

In claim 1, at line 2 of column 6, correct "vestices" to read -- vesicles --.

Signed and Sealed this

Fifteenth Day of October 1985

[SEAL]

Attest:

DONALD J. QUIGG

Attesting Officer

Commissioner of Patents and
Trademarks—Designate